United States Patent
Jordan et al.

(10) Patent No.: US 6,270,982 B1
(45) Date of Patent: Aug. 7, 2001

(54) METHODS AND COMPOSITIONS FOR THE DETECTION OF BACTERIAL ENDOTOXINS

(75) Inventors: Foster T. Jordan, Hollywood; Hui-Ti Chiang; James F. Cooper, both of Charleston, all of SC (US); Norman R. Wainwright, Falmouth, MA (US)

(73) Assignee: Charles River Laboratories, Wilmington, MA (US)

( * ) Notice: Subject to any disclaimer, the term of this patent is extended or adjusted under 35 U.S.C. 154(b) by 0 days.

(21) Appl. No.: 08/947,584

(22) Filed: Oct. 9, 1997

(51) Int. Cl.$^7$ .................... G01N 33/554; G01N 33/53; A61K 39/02; A61K 45/00
(52) U.S. Cl. .................. 435/7.32; 424/184.1; 424/234.1; 424/278.1; 424/282.1; 435/4; 435/7.2; 435/34; 435/184; 435/962; 514/23
(58) Field of Search .................... 424/284.1, 184.1, 424/234.1, 278.1, 282.1; 435/34, 184, 962, 4, 702, 7.32; 514/23

(56) References Cited

U.S. PATENT DOCUMENTS

| | | | |
|---|---|---|---|
| 3,915,805 | 10/1975 | Levin | 195/103.5 |
| 3,944,391 | 3/1976 | Harris et al. | 23/230 |
| 3,954,663 | 5/1976 | Yamamoto et al. | 252/408 |
| 4,038,029 | 7/1977 | Teller et al. | 23/230 |
| 4,038,147 | 7/1977 | Reno | 195/103.5 |
| 4,221,865 | 9/1980 | Dubczak et al. | 435/4 |
| 4,221,866 | 9/1980 | Cotter | 435/4 |
| 4,245,044 | 1/1981 | Kuo et al. | 435/34 |
| 4,273,557 | 6/1981 | Juranas | 23/230 |
| 4,279,774 | 7/1981 | Lindsay et al. | 252/408 |
| 4,301,245 | 11/1981 | Lindsay et al. | 435/4 |
| 4,322,217 * | 3/1982 | Dikeman | 23/230 |
| 4,370,413 | 1/1983 | Neeman et al. | 435/39 |
| 4,376,819 | 3/1983 | Brown et al. | 435/4 |
| 4,606,824 | 8/1986 | Chu et al. | 210/635 |
| 4,717,658 | 1/1988 | Michaels | 435/19 |
| 5,155,032 | 10/1992 | Tanaka et al. | 435/184 |
| 5,179,006 | 1/1993 | Matuura et al. | 435/23 |
| 5,266,461 | 11/1993 | Tanaka | 435/7.21 |
| 5,286,625 | 2/1994 | Tanaka et al. | 435/18 |
| 5,310,657 | 5/1994 | Berzofsky | 435/34 |
| 5,316,911 | 5/1994 | Baek et al. | 435/7.9 |
| 5,318,893 | 6/1994 | Matuura et al. | 435/23 |
| 5,389,547 | 2/1995 | Tanaka et al. | 435/94 |
| 5,401,647 * | 3/1995 | Tanaka et al. | 435/176 |
| 5,474,984 | 12/1995 | Tanaka et al. | 514/23 |
| 5,550,030 | 8/1996 | Tanaka et al. | 435/23 |
| 5,574,023 | 11/1996 | Shibata et al. | 514/54 |
| 5,605,806 | 2/1997 | Tanaka et al. | 435/7.32 |
| 5,637,474 * | 6/1997 | Takaoka et al. | 435/18 |
| 5,681,710 | 10/1997 | Tanaka et al. | 435/13 |
| 5,695,948 | 12/1997 | Tanaka et al. | 435/13 |
| 5,702,882 | 12/1997 | Tamura et al. | 435/4 |
| 5,795,962 * | 8/1998 | Iwanaga et al. | 530/350 |

OTHER PUBLICATIONS

Roslansky et al. J. of Clinical Microbiology 29(11): 2477–2483, 1991.*
Cooper et al. PDA J. of Pharmaceutical Science & Tech 51:2–6 (Jan.–Feb. 1997).*
Obayashi et al. Clin Chin. Acta 149:55–65, 1985.*
Pearson et al, "Comparison of Chemical Analyses of Hollow–Fiber Dialyzer Extracts," *Artificial Organs*, vol. 8, No. 3:291–298 (1984).
Cooper et al., "The Impact of Non–endotoxin LAL–Reactive Materials on Limulus Amebocyte Lysate Analyses," *PDA J. of Pharmaceutical Science & Tech.*: 51:2–6 (Jan.–Feb. 1997).
Obayashi et al., "A new chromogenic endotoxin–specific assay using recombined limulus coagulation enzymes and its clinical applications," *Clin. Chin. Acta* 149:55–65 (1985).
Roslansky et al., "Sensitivity of Limulus Amebocyte Lysate (LAL) to LAL–Reactive Glucans," *J. of Clinical Microbiology*, 29:2477–2483 (1991).
Seki et al., "Horseshoe Crab (1,3)–β–D–Glucan–sensitive Coagulation Factor G," *J. of Biological Chem.* 269:1370–1374 (1994).

* cited by examiner

*Primary Examiner*—Rodney P Swartz
(74) *Attorney, Agent, or Firm*—Testa, Hurwitz & Thibeault, LLP

(57) ABSTRACT

The invention provides methods and compositions for the detection and/or quantification of bacterial endotoxins. In particular, provided herein is an inexpensive and reproducible method for producing an improved amebocyte lysate preparation having reduced Factor G activity. Provided also is an endotoxin-specific amebocyte lysate preparation produced by such a method. In addition, the invention provides methods and compositions for enhancing the sensitivity to endotoxins of amebocyte lysate preparations having reducing Factor G activity. In particular, the sensitivity of such amebocyte lysate preparations to endotoxins can be enhanced by the addition of exogenous (1→3) β-D-glucan.

27 Claims, 5 Drawing Sheets

METHODS AND COMPOSITIONS FOR THE DETECTION OF BACTERIAL ENDOTOXINS

FIELD OF THE INVENTION

This invention relates generally to an amebocyte lysate preparation for use in the detection and/or quantification of a bacterial endotoxin in a sample, and more particularly to an endotoxin-specific amebocyte lysate preparation having reduced Factor G activity for use in the detection and/or quantification of a bacterial endotoxin in a sample.

BACKGROUND OF THE INVENTION

Bacterial endotoxins, also known as pyrogens, are the fever-producing byproducts of Gram negative bacteria and can be dangerous or even deadly to humans. Symptoms of infection may range from fever, in mild cases, to death. In order to promptly initiate proper medical treatment, it is important to identify, as early as possible, the presence of an endotoxin and, if possible, the concentration of the endotoxin in the subject of interest. Similarly, the U.S. Food and Drug Administration (USFDA) requires certain manufacturers to establish that their products, for example, parenteral drugs and medical devices, are free of detectable levels of Gram negative bacterial endotoxin.

To this end, a variety of methods have been developed for use in the detection of bacterial endotoxins. A currently preferred method involves the use of amebocyte lysate (AL) produced from the hemolymph of a horseshoe crab, for example, a horseshoe crab selected from the group consisting of *Limulus polyphemus, Tachpleus gigas, Tachypleus tridentatus,* and *Carcinoscorpius rotundicauda.* Amebocyte lysates produced from Limulus, Tachpleus, and Carcinoscorpius maybe referred to as LAL, TAL, and CAL, respectively.

Presently, LAL is employed in bacterial endotoxin assays of choice because of its sensitivity, specificity and relative ease for avoiding interference by other components that may be present in a sample of interest. LAL, when combined with a sample containing bacterial endotoxin, reacts with the endotoxin to produce a product, for example, a gel or chromogenic product, that can be detected, for example, either visually or by the use of an optical detector.

The endotoxin-mediated activation of LAL is well understood and has been thoroughly documented in the art. See, for example, Levin et al. (1968) Thromb. Diath. Haemorrh. 19: 186, Nakamura et al. (1986) Eur. J. Biochem. 154: 511, Muta et al. (1987) J. Biochem. 101: 1321, and Ho et al. (1993) Biochem. & Mol. Biol. Int. 29: 687. When bacterial endotoxin is contacted with LAL, the endotoxin initiates a series of enzymatic reactions, referred to in the art as the Factor C pathway, that involve at least three serine protease zymogens called Factor C, Factor B and pro-clotting enzyme (see FIG. 1). Briefly, upon exposure to endotoxin, the endotoxin-sensitive factor, Factor C is activated. Activated Factor C thereafter hydrolyses and activates Factor B, whereupon activated Factor B activates proclotting enzyme to produce clotting enzyme. The clotting enzyme thereafter hydrolyzes specific sites, for example, $Arg^{18}$-$Thr^{19}$ and $Arg^{46}$-$Gly^{47}$ of coagulogen, an invertebrate, fibrinogen-like clottable protein, to produce a coagulin gel. See, for example, U.S. Pat. No. 5,605,806.

Although the clotting cascade of LAL initially was considered specific for endotoxin, it was later discovered that (1→3)-B-D glucans also activate the clotting cascade of LAL through a unique enzymatic pathway, referred to in the art as the Factor G pathway (see FIG. 1). Upon exposure to (1→3)-B-D glucan, Factor G is activated to produce activated Factor G. Activated Factor G thereafter converts the proclotting enzyme into clotting enzyme, whereupon the clotting enzyme converts coagulogen into coagulin, similar to the case with endotoxin. Accordingly, the coagulation system of LAL, like the mammalian blood coagulation system, consists of at least two coagulation cascades which include an endotoxin-mediated pathway (the Factor C pathway), and a (1→3)-B-D glucan-mediated pathway (the Factor G pathway). See, for example, Morita et al. (1981) FEBS Lett. 129: 318–321 and Iwanaga et aL (1986) J. Protein Chem. 5: 255–268.

In view of the Factor C and Factor G pathways of LAL, the detection of bacterial endotoxin in a sample can, under certain circumstances, become ambiguous. As a result, attempts have been made to increase the specificity of LAL for endotoxin, i.e., to produce an endotoxin-specific amebocyte lysate preparation.

In one approach, polysaccharide based Factor G inhibitors are combined with amebocyte lysate to reduce or eliminate clotting induced by (1→3)-B-D glucan present in the biological sample, i.e., inhibit the Factor G cascade. See, for example, U.S. Pat. Nos.: 5,155,032; 5,179,006; 5,318,893; 5,474,984; and 5,641,643.

In an alternative approach, several groups have attempted to remove Factor G from LAL thereby to produce a Factor G depleted amebocyte lysate that is insensitive to (1→3)-B-D glucan. For example, Obayashi et al. (1985) Clin. Chim. Acta 149:55–65 disclose a method for fractionating coagulation enzymes in LAL and then recombining only those factors involved in the endotoxin induced coagulation cascade (i.e., the Factor C cascade) to produce a Factor G depleted amebocyte lysate. The resulting lysate, however, may not only lack Factor G but also other components required for a complete Factor C cascade. The reconstituted lysate produced by this procedure, apparently does not produce a natural coagulin type clot and can be used only with synthetic chromogenic substrates.

U.S. Pat. No. 5,401,647 discloses a method for removing Factor G from LAL by combining LAL with (1→3)-B-D glucan immobilized on an insoluble carrier. Once bound to the carrier via the (1→3)-B-D glucan moiety, the Factor G can thereafter be removed from the LAL to produce a Factor G depleted lysate. Similarly, U.S. Pat. No. 5,605,806 discloses an immunoaffinity based method using a Factor G specific antibody to remove Factor G from LAL thereby to produce a Factor G depleted amebocyte lysate.

There still exists, however, a demand for an endotoxin-specific amebocyte lysate that can be produced economically in commercial quantities. A method for producing such an amebocyte lysate should be rapid, reproducible, inexpensive, simple to conduct, and preferably should result in an amebocyte lysate that can be used in a reliable, and quantitative determination of endotoxin in a sample of interest.

SUMMARY OF THE INVENTION

The invention features improved amebocyte lysate preparations having reduced Factor G activity, methods of making such lysate preparations, and methods of using such lysate preparations in the detection and/or quantitation of one or more bacterial endotoxins in a sample of interest.

In one aspect, the invention provides a method of producing an endotoxin-specific amebocyte lysate preparation for use in the detection of bacterial endotoxins in a sample. The amebocyte lysate preparation is rendered endotoxin-specific by the reduction and/or elimination of Factor G activity in the preparation. The amebocyte lysate preparation of the invention is produced by (a) admixing crude amebocyte lysate, i.e., amebocyte lysate reactive with both endotoxin and (1→3)-B-D glucan, with a surfactant in an amount sufficient to produce a solution containing a precipitate; and (b) separating the precipitate from the solution thereby to produce an amebocyte lysate preparation which is less reactive with a (1→3)-β-D glucan than is the crude amebocyte lysate. The precipitate produced by addition of surfactant to crude lysate may contain any component necessary for a complete Factor G cascade, however, the production of a precipitate actually containing Factor G is preferred.

The amebocyte lysate preparation produced by the methodologies described herein comprises all the components necessary for a complete Factor C cascade, i.e., is still capable of producing a coagulin gel via the endotoxin-mediated pathway. Accordingly, the resulting amebocyte lysate preparation is capable of reacting with a bacterial endotoxin, e.g., a bacterial endotoxin produced by Gram negative bacteria, to produce a coagulin clot.

It is contemplated that any surfactant (otherwise known as a surface active agent or detergent) which produces a precipitate when added to crude amebocyte lysate, wherein the precipitate once removed from the lysate results in a reduction of Factor G activity, may be used in the practice of the invention. The surfactant, however, preferably is a zwitterionic surfactant, i.e., a surfactant having a headgroup containing both a negatively charged chemical moiety and a positively charged chemical moiety. Examples of zwitterionic surfactants include betaines and sulfobetaines, however, sulfobetaine-type surfactants are preferred. Preferred sulfobetaine-type surfactants include, without limitation, n-octyl- N, N-dimethyl-3-ammonio-1-propanesulfonate; n-decyl-N, N-dimethyl-3-ammonio-1-propanesulfonate; n-dodecyl-N, N-dimethyl-3-ammonio-1-propanesulfonate; n-tetradecyl-N, N-dimethyl-3-ammonio-1-propanesulfonate; and n-hexadecyl-N, N-dimethyl-3-ammonio-1-propanesulfonate. The sulfobetaine-type surfactant n-tetradecyl-N, N-dimethyl-3-ammonio-1-propanesulfonate, however, is most preferred.

In one embodiment, the method comprises the additional step of removing from or otherwise reducing the concentration of the added surfactant in the solution. The surfactant may be removed, for example, by chromatographic separation using, for example, a suitable ion exchange resin or, alternatively, by any other means known in the art for removing a particular surfactant from an aqueous solution. In a preferred method, the surfactant is removed by conventional organic solvent extraction. Any organic solvent that dissolves the surfactant of interest and is compatible with amebocyte lysate may be used in the solvent extraction step, however, for the reasons discussed below, chloroform is preferred.

In another embodiment, the sensitivity to bacterial endotoxin of an amebocyte lysate preparation having reduced Factor G activity can be enhanced by the addition of exogenous (1→3)-β-D glucan to the amebocyte lysate preparation. In particular, (1→3)-β-D glucan is added to the lysate preparation in an amount sufficient to enhance the sensitivity of the lysate preparation to endotoxin relative to a similar amebocyte lysate preparation without exogenously added (1→3)-β-D glucan. Without wishing to be bound by theory, it appears that exogenously added (1→3)-β-D glucan acts synergistically with the endotoxin mediated pathway. It is understood, however, that the same amount of (1→3)-β-D glucan when added to crude amebocyte lysate, i.e., amebocyte lysate that is reactive with both endotoxin and (1→3)-β-D glucan, likely would induce the production of a coagulin gel via the Factor G cascade. In effect, during the practice of this particular embodiment of the invention, a substrate or initiator of the Factor G cascade is added to the amebocyte lysate preparation of the invention.

Although it is contemplated that any amount of (1→3)-β-D glucan that enhances the sensitivity of the amebocyte lysate to the endotoxin relative to similar amebocyte lysate without the exogenously added (1→3)-β-D glucan may be used in the practice of the invention, the optimal amount of exogenous (1→3)-β-D glucan for enhancing the endotoxin-specific cascade in a particular lysate can be determined by routine experimentation. For example, the optimal concentration can be determined by adding different amounts of a particular (1→3)-β-D glucan to crude amebocyte lysate, i.e., amebocyte lysate reactive with both endotoxin and (1→3)-β-D glucan. The optimal amount of the (1→3)-β-D glucan to be added to the amebocyte lysate preparation of the invention, can be determined using, for example, a kinetic turbidimetric assay whereby the optimal amount is the amount of (1→3)-β-D glucan that induces the fastest coagulin clot formation in crude amebocyte lysate. This assay protocol is exemplary, and it is understood that the skilled artisan may use a variety of other assays, for example, a gelclot assay, an end-point turbidimetric assay, or a chromogenic assay, to determine the optimal amount of (1→3)-β-D glucan to be added to the lysate of interest.

It is contemplated that any (1→3)-β-D glucan that induces the Factor G cascade in crude amebocyte lysate can be used to enhance the sensitivity of the endotoxin mediated pathway in the amebocyte lysate preparation of the invention. Preferred (1→3)-β-D glucans include, without limitation, cotton extract; rinses from cellulose acetate membranes; curdlan; pachyman; scleratan; leutinan; schizophyllan; coriolan; laminaran; and laminarin. Laminarin, however, currently is most preferred.

In another aspect, the invention provides an amebocyte lysate preparation having reduced Factor G activity, i.e., an amebocyte lysate having reduced reactivity to (1→3)-β-D glucans relative to crude lysate produced by the aforementioned methodologies. In one embodiment, such a composition may comprise (i) an amebocyte lysate preparation having reduced Factor G activity or, most preferably, an amebocyte lysate preparation depleted of Factor G activity, and (ii) exogenously added (1→3)-β-D glucan, wherein the (1→3)-β-D glucan is added in an amount sufficient to enhance the sensitivity of the amebocyte lysate preparation to endotoxin relative to a similar amebocyte lysate preparation without the exogenously added (1→3)-β-D glucan. Determination of the optimal amount of a particular (1→3)-β-D glucan for enhancing sensitivity of the lysate to endotoxin has been discussed previously.

In another aspect, the invention provides methods for detecting and/or quantitating the amount of a bacterial endotoxin in a sample. The improvement in such methods resides in the use of the amebocyte lysate preparation of the invention.

The foregoing and other objects, features and advantages of the present invention will be made more apparent from the following detailed description of preferred embodiments of the invention.

BRIEF DESCRIPTION OF THE DRAWINGS

The objects and features of the invention may be better understood by reference to the drawings described below in which.

DETAILED DESCRIPTION OF THE INVENTION

Figure 1:
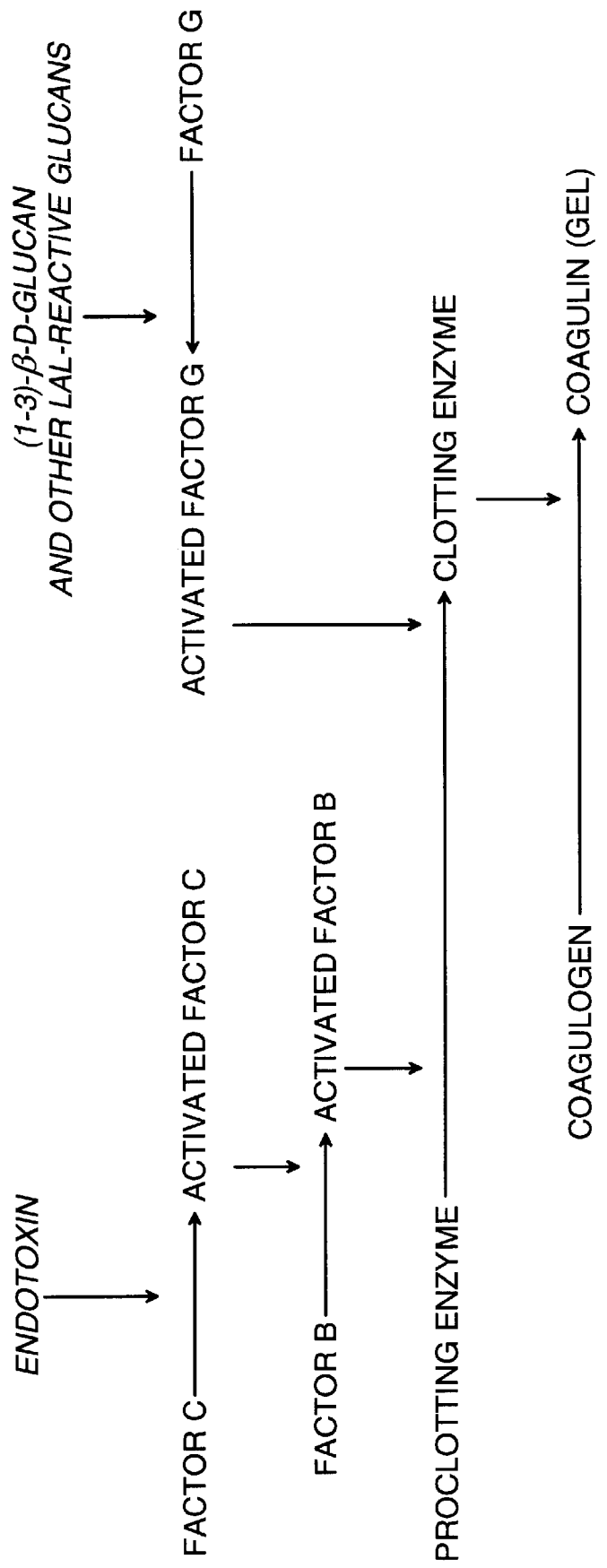
FIG. 1 is a schematic representation of the blood coagulation system of horseshoe crab amebocytes.
Figure 2:
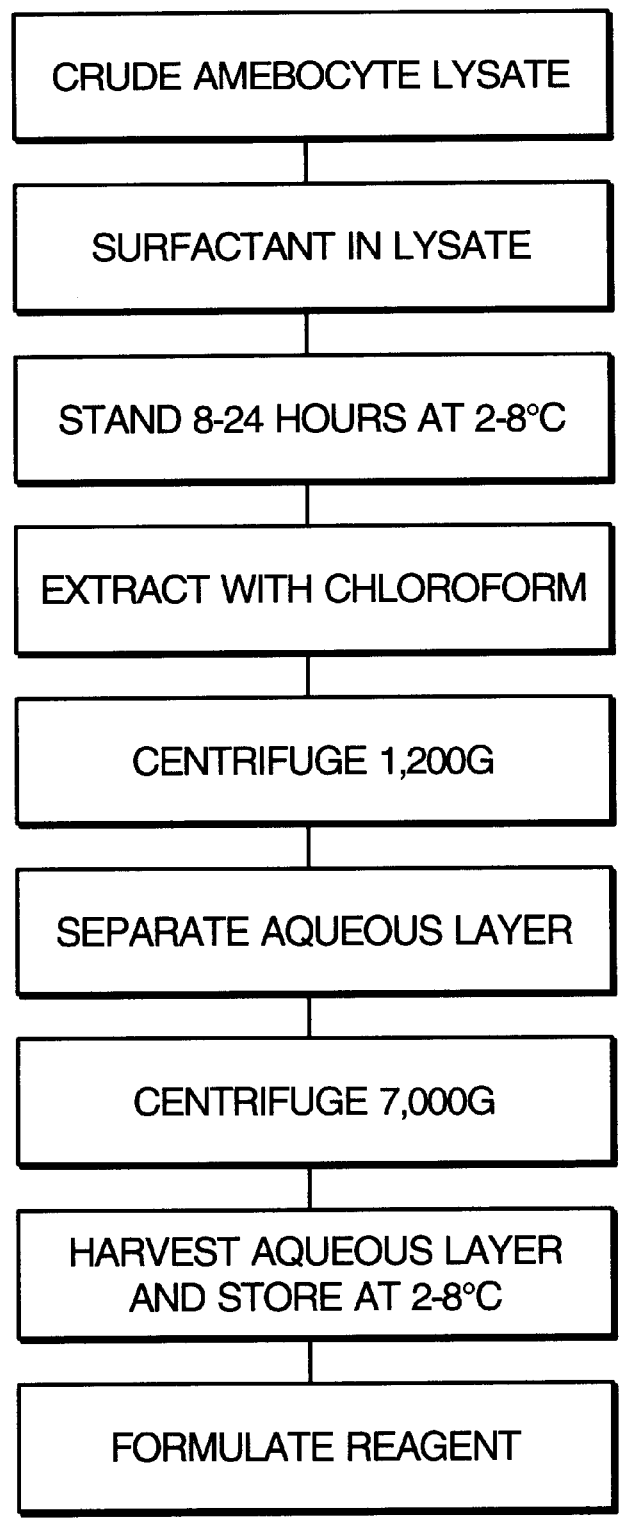
FIG. 2 is a flow chart showing an exemplary protocol for producing an amebocyte lysate preparation having reduced Factor G activity.

As will be more fully described below, this invention is based, in part, upon the discovery of an inexpensive and reliable method for producing an endotoxin-specific amebocyte lysate preparation. The resulting amebocyte lysate preparations are useful in the detection and/or quantitation of a bacterial endotoxin in a sample of interest.

In particular, the method is based upon a protocol for reducing or preferably depleting amebocyte lysate of Factor G activity, with the resulting lysate being less reactive to (1→3)-β-D glucan than untreated amebocyte lysate. In addition, the invention is based, in part, upon the discovery that (1→3)-β-D glucan, when exogenously added to an amebocyte lysate preparation depleted of Factor G activity (for example, by the removal of Factor G, or by the addition of Factor G inhibitors, for example, Factor G inhibitors of the type described in U.S. Pat. Nos. 5,155,032; 5,179,006; 5,318,893; 5,474,984; and 5,641,643, the disclosures of which are incorporated herein by reference) can enhance the sensitivity of the resulting amebocyte lysate preparation to endotoxin. The invention, therefore, provides an endotoxin-specific amebocyte lysate preparation for use in reliably detecting and/or quantitating a bacterial endotoxin in a sample of interest.

The amebocyte lysate preparation of the invention is produced by: (a) admixing a sample of crude amebocyte lysate, i.e., amebocyte lysate that is reactive with both endotoxin and (1→3)-β-D glucan, with a surfactant in an amount sufficient to produce a solution containing a precipitate; and (b) separating the precipitate from the solution thereby to produce an amebocyte lysate preparation which is less reactive with a (1→3)-β-D glucan than the crude amebocyte lysate. The resulting amebocyte lysate preparation preferably still comprises all components necessary for the Factor C cascade and, therefore, is capable of producing a coagulin gel following the addition of endotoxin.

As used herein, the term, "amebocyte lysate" is understood to mean any lysate produced by the lysis of blood cells (amebocytes) extracted from the hemolymph of a horseshoe crab. Preferred horseshoe crabs include crabs belonging to the Limulus genus, for example, *Limulus polyphemus*, the Tachpleus genus, for example, *Tachpleus gigas*, and *Tachypleus tridentatus*, and the Carcinoscorpius genus, for example, *Carcinoscorpius rotundicauda*. As used herein, the term, "crude amebocyte lysate" is understood to mean any amebocyte lysate that is capable of producing a coagulin clot in the presence of an endotoxin, for example, an endotoxin produced by Gram negative bacteria, and a (143)-β-D glucan, for example, laminarin.

As used herein, the term, "Factor G" is understood to mean any protein or polypeptide that acts as a serine protease zymogen and is capable of initiating the production of a coagulin gel-clot in crude amebocyte lysate following exposure to (1→3)-β-D glucan. The isolation and characterization of horseshoe crab Factor G has been discussed extensively in the art (see, for example, Seki et al. (1994) J. Biol. Chem. 269: 1370–1374, the disclosure of which is incorporated herein by reference) and, therefore, is not discussed in detail herein.

As used herein, the term, "(1→3)-β-D glucan" is understood to mean any water soluble polysaccharide, disaccharide or derivative thereof that is (i) capable of inducing formation of a coagulin clot in crude Limulus amebocyte lysate, and (ii) contains at least two β-D glucosides, as defined in formula I below, connected by a (1→3)-β-D glycosidic linkage. It is contemplated that such a polysaccharide or derivative thereof, in addition to containing a (1→3)-β-D glycosidic linkage may also contain glucoside moieties connected by a variety of other glycosidic linkages, for example, via a (1→4)-β-D glycosidic linkage and/or by a (1→6)-β-D glycosidic linkage. It is contemplated that such (1→3)-β-D glucans may be isolated from a variety of sources including, without limitation, plants, bacteria, yeast, algae, and fungi, or alternatively may be synthesized using conventional sugar chemistries.

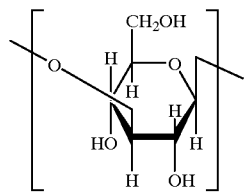

Formula I

As used herein, the term "reactive with (1→3)-β-D glucan" refers to an amebocyte lysate, which in the presence of a (1→3)-β-D glucan is capable of producing a product that can be detected in a conventional gel-clot assay, end point-turbidimetric assay, kinetic turbidimetric assay or a chromogenic assay. Similarly, as used herein, the term "reactive with a bacterial endotoxin" refers to an amebocyte lysate, which in the presence of an endotoxin produced by a Gram negative bacteria is capable of producing a product that can be detected in a conventional gel-clot assay, end point-turbidimetric assay, kinetic turbidimetric assay or a chromogenic assay.

As used herein, the term, "surfactant" is understood to mean any surface active agent or detergent that is capable of producing a precipitate when admixed with crude amebocyte lysate, wherein the precipitate once removed from the lysate results in a reduction of Factor G activity. As used herein, the term, "zwitterionic surfactant" is understood to mean any surfactant having a headgroup containing both a negatively charged chemical moiety and a positively charged chemical moiety. Examples of useful zwitterionic surfactants useful in the practice of the instant invention include, without limitation, betaines (see, for example, formula II below) and sulfobetaines (see, for example, formula III below), however, sulfobetaines currently are the most preferred.

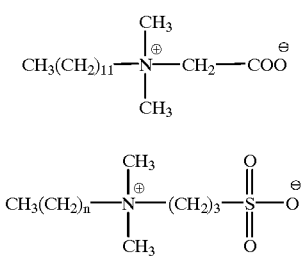

Formula II

Formula III wherein n can be 7, 9, 11, 13 or 15.

As used herein, the term, "precipitate" is understood to mean any insoluble material produced following admixture of crude amebocyte lysate with a surfactant. It is contemplated that the precipitate may contain Factor G and/or other, heretofore undiscovered, components necessary for a functional Factor G cascade.

Preparation of Amebocyte Lysate having Reduced Factor G Activity

A flow chart showing an exemplary protocol for producing an amebocyte lysate preparation having reduced Factor G activity, more preferably, an amebocyte lysate preparation depleted of Factor G activity is shown in FIG. 1. It is contemplated that any crude amebocyte lysate may be used as a starting material in the protocol shown in FIG. 1.

Crude lysates may be produced using the procedure as originally described in Levin et al. (1968) Thromb. Diath. Haemorrh. 19:186, with modification. Briefly, blood (hemolymph) is harvested from horseshoe crab in a saline solution isotonic with sea water (about 3% NaCl (w/v)) containing an anti-coagulant, for example, N-ethylmaleimide, caffeine, or Tween®. The amebocytes are washed with the same solution to remove hemolymph factors and lysed by osmotic shock via exposure to pyrogen-free water. After 24 hours, the amebocyte lysate is separated from cellular debris by centrifugation. The preparation of crude lysate also is discussed, for example, in Richard B. Prior, Ed., "Clinical Applications of the Limulus Amebocyte Lysate Test" CRC Press, pp. 28–36 and pp. 159–166, and in U.S. Pat. No. 4,322,217, the disclosures of which are incorporated herein by reference.

In order to produce amebocyte lysate having reduced Factor G activity, surfactant is added to crude amebocyte lysate in an amount sufficient to produce a precipitate. As mentioned previously, it is contemplated that any surfactant or detergent which produces a precipitate upon addition to crude amebocyte lysate, wherein the precipitate once removed from the lysate results in a reduction of Factor G activity, may be used in the practice of the invention. Preferred surfactants include zwitterionic surfactants, i.e., surfactants having a headgroup containing both a negatively charged chemical moiety and a positively charged chemical moiety. Examples of zwitterionic surfactants useful in the practice of the invention include betaines and sulfobetaines, however, sulfobetaine-type surfactants are the more preferred.

A family of sulfobetaine type detergents are available commercially from Calbiochem®, San Diego, Calif. under the tradename Zwittergent®. Sulfobetaine type detergents apparently retain zwitterionic character over a wide pH range. Currently preferred sulfobetaine-type surfactants include, without limitation, n-octyl- N, N-dimethyl-3-ammonio-1-propanesulfonate (also known as Zwittergent® 3–08); n-decyl-N, N-dimethyl-3-ammonio-1-propanesulfonate (also known as Zwittergent® 3–10); n-dodecyl-N, N-dimethyl-3-ammonio-1-propanesulfonate (also known as Zwittergent® 3–12); n-tetradecyl-N, N-dimethyl-3-ammonio-1-propanesulfonate (also known as Zwittergent® 3-14); and n-hexadecyl-N, N-dimethyl-3-ammonio-1-propanesulfonate (also known as Zwittergent® 3–16). The sulfobetaine-type surfactant is n-tetradecyl-N, N-dimethyl-3-ammonio-1-propanesulfonate (Zwittergent® 3–14), however, is most preferred.

The optimal concentration of surfactant necessary to produce a precipitate when combined with crude amebocyte lysate can be determined by routine experimentation. For example, the skilled artisan may simply add increasing concentrations of a particular surfactant to crude amebocyte lysate until a precipitate is produced. The amebocyte lysate preparation following removal of the precipitate can then be tested for reduced Factor G activity using any of the conventional assays, for example, gel-clot, end-point turbidimetric, kinetic turbidimetric, or chromogenic assays, well known and thoroughly document in the art. With regard to the sulfobetaine type-detergents, preferred detergent concentrations range from about 0.01% to about 0.6% (w/v) and most preferably from about 0.05% to about 0.25% (w/v). Specifically, with regard to the sulfobetaine-type surfactant n-tetradecyl-N, N-dimethyl-3-ammonio-1-propanesulfonate (Zwittergent® 3–14), this detergent is preferably added to the crude lysate to a final concentration of from about 0.05% (w/v) to about 0.20% (w/v), most preferably about 0.12% (w/v) to produce a precipitate.

Optimal precipitation conditions may be determined by varying one or more of detergent concentration, temperature, and time of incubation. For example, preferred incubation conditions include incubation at temperatures below about 20° C., most preferably about 2–15° C. for about 2–24 hours. These conditions appear to preserve the activity of the lysate preparation during the precipitation step. For example, in the case of Zwittergent® 3–14, the resulting mixture preferably is incubated at 2–8° C. for 8–24 hours. Following incubation, the resulting precipitate can be removed by any conventional technique known in the art, for example, centrifugation followed by the removal of supernatant from a pellet of precipitate.

In a preferred embodiment, the concentration of the surfactant remaining in the supernatant, if necessary, is reduced to a level that permits the Factor C cascade to be operative. The extent of surfactant removal to produce a lysate containing an operative Factor C cascade may be determined by routine experimentation. For example, the amount of surfactant remaining in the supernatant can be determined, for example, by standard thin layer chromatography (TLC). Under certain circumstances it may be preferable to remove at least about 35% of the surfactant from the supernatant, more preferably at least about 70%, and most preferably at least about 90%. For example, consistent removal of at least about 90% of the surfactant from the lysate, enables one to produce formulations of amebocyte lysate preparations with relatively defined components. As a result, it may be easier to produce batches of amebocyte lysate preparations having the same or similar activities. It is understood, however, that it is possible to control the sensitivity of the resulting lysate preparation to endotoxin by altering the concentration of residual detergent in the lysate preparation. For example, the more detergent removed, the more sensitive the lysate to endotoxin. Accordingly, in order to prepare a lysate having a desired sensitivity to endotoxin, the amount of detergent removed from the lysate preparation may be altered by varying the detergent extraction conditions discussed below.

It is contemplated that the skilled artisan may use any conventional procedure for removing a particular surfactant or more particularly, Zwittergent® from the mixture. For example, it is contemplated that the surfactant may removed by, for example, conventional ion exchange chromatography or, more preferably by organic solvent extraction. Furthermore, it is contemplated that the surfactant may be removed prior to, subsequent to, or during the removal of the precipitate from the mixture.

In a preferred embodiment, Zwittergent® surfactant is removed from the mixture simultaneously with the precipitate by organic solvent extraction. For example, following the production of the precipitate, the resulting mixture may be extracted with an organic solvent that dissolves surfactant and is compatible with amebocyte lysate. In an exemplary protocol, organic solvent is added to the mixture of amebocyte lysate and surfactant, and the combination thoroughly mixed. After extraction, the combination may separate to produce a three phase system comprising an organic phase, an interface of precipitate, and an aqueous phase. When an organic solvent, for example, chloroform is employed, the resulting aqueous phase is located above the organic phase, with the precipitate residing at the interface of the organic and aqueous phases.

It is contemplated that any organic solvent which dissolves the surfactant and which is compatible with amebocyte lysate (i.e., does not impair the Factor C cascade) may be used to remove the surfactant. Also, it has been noted that certain organic solvents may be used to remove or inactivate lysate inhibitors, which when removed or inactivated enhance the sensitivity of the resulting lysate to endotoxin. See, for example, U.S. Pat. Nos. 4,107,077 and 4,279,774, the disclosures of which are incorporated herein by reference. Accordingly, it may be preferable, but not essential that the organic solvent used to remove the surfactant also remove or inactive the lysate inhibitors. Preferred solvents include, without limitation, chloroform, iodoform, bromoform, lower alkyl halides such as methyl bromide, methyl chloride, methyl iodide, ethyl chloride, ethyl iodide, propyl chloride, propyl bromide and propyl iodide, ethylene dichloride, methylene dichloride, benzene, monohalobezenes such as chlorobenzene, bromobenzene and iodobenzene, lower alkyl ethers such as dimethyl ether and diethyl ether, carbon tetrachloride, trichloroethane, trichloroethylene, toluene and hexane. Choice of the optimal organic solvent for a particular surfactant may be determined by routine experimentation In a preferred embodiment, when using the sulfobetaine detergent Zwittergent® 3–14, chloroform is the preferred organic solvent for use in the organic extraction. Chloroform is not only compatible with the lysate and capable of dissolving Zwittergent® 3–14, but also is capable of removing and/or inactivating known LAL inhibitors in amebocyte lysate. It is understood that the amount of detergent removed can be altered, thereby altering the endotoxin sensitivity of the lysate, by varying the chloroform to lysate ratio during organic solvent extraction.

Following extraction, the resulting organic and aqueous phases are allowed to separate. Separation may be speeded up by centrifugation. For example, phase separation may be speeded up by centrifugation at about 500 G to about 2,000 G, most preferably about 1,200 G. Following centrifugation, the aqueous phase is harvested. For example, when chloroform is used, the upper aqueous phase may be harvested by decanting the aqueous phase thereby leaving behind the interfacial material and the lower chloroform organic phase. The decanted upper aqueous phase, preferably is subjected to a second round of centrifugation, for example, at about 5,000 G to about 9,000 G, most preferably about 7,000 G. The resulting aqueous phase then is separated and harvested from residual interfacial material and/or organic phase, and either stored or formulated as desired. It is appreciated, however, that the optimal number and extent of the centrifugation steps for a particular system may be determined by routine experimentation.

The resulting upper aqueous phase can then stored at reduced temperature or formulated immediately. For example, when frozen lysate may retain activity indefinitely, whereas, when stored at 2–8° C., the lysate may retain activity for several weeks. The reduction in Factor G activity of the resulting amebocyte lysate preparations can be determined using any of the techniques described hereinbelow.

Enhancement of the Sensitivity of Amebocyte Lysate Preparations to Endotoxin.

As discussed hereinabove, it has been discovered that the sensitivity to endotoxin of an amebocyte lysate preparation having reduced Factor G activity may be enhanced by the addition of an exogenous (1→3)-β-D glucan. An increase in sensitivity is understood to mean that the lysate with additive reacts faster to produce a product at lower endotoxin concentrations than lysate without additive. In particular, (1→3)-β-D glucan can be added to the lysate preparation in an amount sufficient to enhance the endotoxin sensitivity of the lysate preparation relative to a similar amebocyte lysate preparation without the exogenously added (1→3)-β-D glucan. It is understood, however, that the same amount of (1→3)-β-D glucan when added to crude amebocyte lysate likely would induce the production of a coagulin gel via the Factor G cascade. In effect, during the practice of this particular embodiment of the invention, surprisingly a substrate or initiator of the now reduced or depleted Factor G cascade is added to the amebocyte lysate preparation of the invention. It is contemplated that this type of enhancement may occur with any lysate depleted of Factor G activity (e.g., wherein Factor G is removed from lysate or wherein the lysate contains Factor G inhibitors).

The identification of suitable (1→3)-β-D glucans as well as the identification of optimal concentrations of (1→3)-β-D glucans for enhancing endotoxin sensitivity may be determined by routine experimentation using the methodologies described hereinbelow. With regard to the type of useful (1→3)-β-D glucans, it is contemplated that any (1→3)-β-D glucan that induces a Factor G mediated cascade in crude amebocyte lysate can be used in the practice of this aspect of the invention. Currently preferred (1→3)-β-D glucans include, without limitation, natural polysaccharides obtained from cell walls of, for example, various bacteria (for example, Alcaligenes genus, and Agrobacterium genus), yeasts (for example, shiitake) with specific examples of natural polysaccharides including, for example, curdlan, pachyman, scleratan, leutinan, schizophylan, and coriolan. Other natural polysaccharides include storage polysaccharides of algae, for example, brown algae, Euglena, diatoma, with specific examples of storage polysaccharides including, for example, laminaran, laminarin, and paramilon. Preferred (1→3)-β-D glucans also include, for example, polysaccharide derivatives in which at least one group selected from a carboxymethyl group, a carboxyethyl group, a methyl group, a hydroxyethyl group, a hydroxypropyl group, and a sulfopropyl group, is introduced into a natural polysaccharide or storage polysaccharide using conventional methodologies well known in the art. See, for example, Munio Kotake "Daiyukikagaku" Vol. 19 7$^{th}$ ed. Asakura Shoten, May 10 (1967) pp. 70–101; A. E. Clarke et al. (1967) Phyto-chemistry 1: 175–188; and T. Sasaki et al. (1967) Europ. J. Cancer, 15: 211–215. Other naturally occurring polysaccharides may be derived from cotton wool, for example, in cotton wool extracts, and certain cellulose-based filters used in the processing of medicinals. See, for example, Roslansky et al. (1991) J. Clin. Micro. 29: 2477; Henne et al. (1984) Artif. Organs 8: 299; and Ikemura et al. (1989) J. Clin. Micro. 27: 1965. Furthermore, it is contemplated that the aforementioned polysaccharides and derivatives thereof may be used either alone or in combination with others to enhance endotoxin sensitivity.

Although it is contemplated that any amount of (1→3)-β-D glucan that enhances the sensitivity of the amebocyte lysate to the endotoxin relative to similar amebocyte lysate without the exogenously added (1→3)-β-D glucan can be used in the practice of this aspect of the invention, the optimal amount of exogenous (1→3)-β-D glucan for enhancing the endotoxin-specific cascade in a particular lysate can be determined by routine experimentation. For example, the optimal concentration can be determined by adding different amounts of a particular (1→3)-β-D glucan to crude amebocyte lysate, wherein the optimal amount is the amount of (1 →3)-β-D glucan that induces the fastest coagulin clot or color formation in crude amebocyte lysate. See, for example, Examples 4, 5 and 6, disclosed hereinbelow. These assay protocols are considered to be exemplary, and it is understood that the skilled artisan may use a variety of assays, for example, gel-clot, kinetic turbidimetric, end-point turbidimetric or chromogenic assays, to determine the optimal amount of (1→3)-β-D glucan to be added to the lysate of interest.

Once the optimal concentration of a particular (1→3)-β-D glucan for enhancing endotoxin sensitivity has been determined, then the same of amount of the (1→3)-β-D glucan can then be added to an amebocyte lysate preparation having reduced or eliminated Factor G activity thereby to enhance the endotoxin sensitivity of the resulting mixture. It is contemplated that the endotoxin sensitivity of any amebocyte lysate having reduced Factor G activity may be enhanced by the addition of (1→3)-β-D glucan. For example, it is contemplated that the endotoxin sensitivity of any amebocyte lysate having reduced Factor G activity may be enhanced by the addition of exogenous (1→3)-β-D glucan.

Formulation of Amebocyte Lysate

The resulting lysate may be formulated using conventional methodologies well known and thoroughly discussed in the art. See, for example, R. B. Prior, Ed., (1990), "Clinical Applications of the Limulus Amebocyte Lysate Test", CRC Press, and U.S. Pat. No. 4,322,217, the disclosures of which are incorporated herein by reference. Methods for enhancing sensitivity of amebocyte lysate may include, without limitation, the aging of crude amebocyte lysate, adjustment of pH, adjustment of divalent cation concentration, adjustment of coagulogen concentration, chloroform extraction, and the addition of serum albumin, biocompatible buffers and/or biological detergents.

For example, typical formulation additives may include, without limitation, about 100–300 mM NaCl, about 10–100 mM divalent cations (e.g., $Mg^{2+}$ or $Ca^{2+}$), biocompatible buffers, e.g., Tris, to give a final pH of about 6.0 to 8.0, and, if the lysate is to be freeze dried, then sugars, e.g., mannitol or dextran. It is contemplated that, the choice of appropriate formulation additives may be determined by routine experimentation.

Lysate, once formulated, typically is lyophilized for long term storage. The lyophilized amebocyte lysate formulations may be reconstituted prior to use by the addition of, for example, pyrogen-free water, or any other pyrogen-free biocompatible buffer.

Methods for Measuring Bacterial Endotoxins

It is contemplated that the amebocyte lysate preparations of the invention may be used to detect and/or quantitate the amount of endotoxin in any sample of interest. For example, it is contemplated that the lysate may be used to detect and/or measure the concentration of endotoxin in any pharmaceutical preparation, for example, an organically produced drug or a recombinantly produced protein, and/or any medical device of interest. In addition, the lysate may be used to detect and/or measure the concentration of endotoxin in biological samples of, for example, blood, serum, plasma, urine, semen, ascitic fluid, peritoneal fluid, sputum, breast exude, and spinal fluid.

It is contemplated that the amebocyte lysate of the invention may be used to detect and/or quantitate a bacterial endotoxin in a sample using any lysate-based assay now known or later developed that detects one or more products of the Factor C cascade. It is contemplated, however, that the amebocyte lysate preparation of the invention may be used to advantage in any conventional gel-clot, end-point turbidimetric, kinetic turbidimetric, or chromogenic assay, known and/or used in the art. The particulars of each of these four types of assays are described below.

(i) Gel-Clot Assay

This technique is described in Prior, R. B., Ed., supra, pp. 28–34, the disclosure of which is incorporated by reference herein, and, therefore, is not described in detail herein. Briefly, the gel-clot assay comprises the steps of (i) mixing amebocyte lysate preparation with the sample to be analyzed, (ii) incubating the resulting mixture at a temperature of 0° to 40° C., preferably 25° to 40° C., for a predetermined time, for example, one hour, and (iii) visually inspecting whether or not a gel-clot has been produced.

(ii) End Point Turbidimetric Assay

This technique is described in Prior, R. B., Ed., supra, pp. 28–34 and, therefore, is not described in detail herein. Briefly, the end point turbidimetric assay comprises the steps of (i) mixing amebocyte lysate preparation with a sample to be investigated, (ii) incubating the resulting mixture at a temperature of 0° to 40° C., preferably 25° to 40° C., for a predetermined time, and (iii) measuring the increase in turbidity as a result of in coagulation, if any, using a conventional coagulometer, nepherometer, spectrophotometer, or the like.

(iii) Kinetic Turbidimetric Assay

This technique is described in Prior, R. B., Ed., supra, pp. 28–34 and, therefore, is not described in detail herein. Briefly, the kinetic turbidimetric assay comprises the steps of (i) mixing amebocyte lysate preparation with a sample to be investigated, (ii) incubating the resulting mixture at a temperature of 0° to 40° C., preferably 25° to 40° C., over a predetermined time range, and (iii) measuring a time required for either a turbidity change caused by coagulation to reach a preselected value or a ratio in change of the turbidity, using a conventional coagulometer, nepherometer, spectrophotometer, or the like.

(iv) Chromogenic Assay

This technique is described in Prior, R. B., Ed., supra, pp. 28–34, and U.S. Pat. Nos.: 4,301,245; 4,717,658; and 5,310,657, the disclosures of which are incorporated herein by reference and, therefore, is not described in detail herein. Briefly, the chromogenic assay comprises the steps of (i) mixing amebocyte lysate preparation with a sample to be investigated, (ii) incubating the resulting mixture at a temperature of 0° to 40° C., preferably 25° to 40° C., for a predetermined time, then, if necessary, adding a reaction inhibitor, and (iii) measuring a substance released by protease activity from the synthetic substrate calorimetrically, or the like.

EXAMPLES

Practice of the invention will be more fully understood from the following examples, which are presented herein for illustrative purposes only, and should not be construed as limiting the invention in any way.

Example 1

Preparation and Characterization of Amebocyte Lysate Depleted of Factor G Activity This example describes a preferred method for producing an amebocyte lysate having reduced Factor G activity. Throughout the following procedure, all reagents and apparatus, where appropriate, are produced or treated to be pyrogen free. Such methodologies are well known in the art and, therefore, are not discussed in detail herein. For example, apparatus may be made pyrogen-free by baking in an oven at ≧200° C. for four hours, and reagents may be made pyrogen-free by treatment by ultra filtration (≦20 kD cut off), oxidation with peroxide, or treatment with NaOH.

Crude amebocyte lysate was prepared by harvesting hemolymph from horseshoe crab. The resulting hemolymph was centrifuged to produce an amebocyte pellet. The amebocytes then were reharvested, rerinsed and recentrifuged. After second rinsing and harvesting steps, the resulting amebocytes were lysed by osmotic shock, and the resulting crude amebocyte lysate stored at 2–8° C. until further use.

Thereafter, Zwittergent® 3–14 was added stepwise to the crude lysate to a final concentration of 0.12% (w/v). The resulting solution was stored at 2–8° C. for 8–24 hours. Thereafter, the solution was mixed with chloroform (4–5 parts lysate to 1 part chloroform) by gentle stirring for 10–30 minutes at 2–8° C. The resulting mixture was then centrifuged at 1,200 G for 15 minutes, whereupon the resulting upper aqueous and lower organic phases were separated by interfacial precipitate material. The aqueous phase then was harvested by decanting, and recentrifuged at 7,000 G for at least 30 minutes to achieve clarity. After centrifugation, the resulting aqueous phase was decanted from the residual organic phase and interfacial material. The extent of detergent extraction was estimated by thin layer chromatography (TLC). Briefly, samples of chloroform extract and lysate were applied to a TLC plate (Whatman PE SIL GLUV), developed with methanol:water (10:1(v/v)), and the detergent visualized with UV light. By this procedure, no residual detergent was detectable in the lysate.

Fractionation of the crude amebocyte lysate, the precipitate produced by the surfactant, and the supernatant containing the amebocyte lysate by sodium dodecyl sulfate polyacrylamide gel electrophoresis (SDS-PAGE) suggests that Factor G is actually contained in the precipitate and, therefore, is removed from the lysate. Densitometric profiles of each lane of the resulting Coomassie Blue stained SDS-PAGE gel are shown in FIG. 3.

Figure 3:
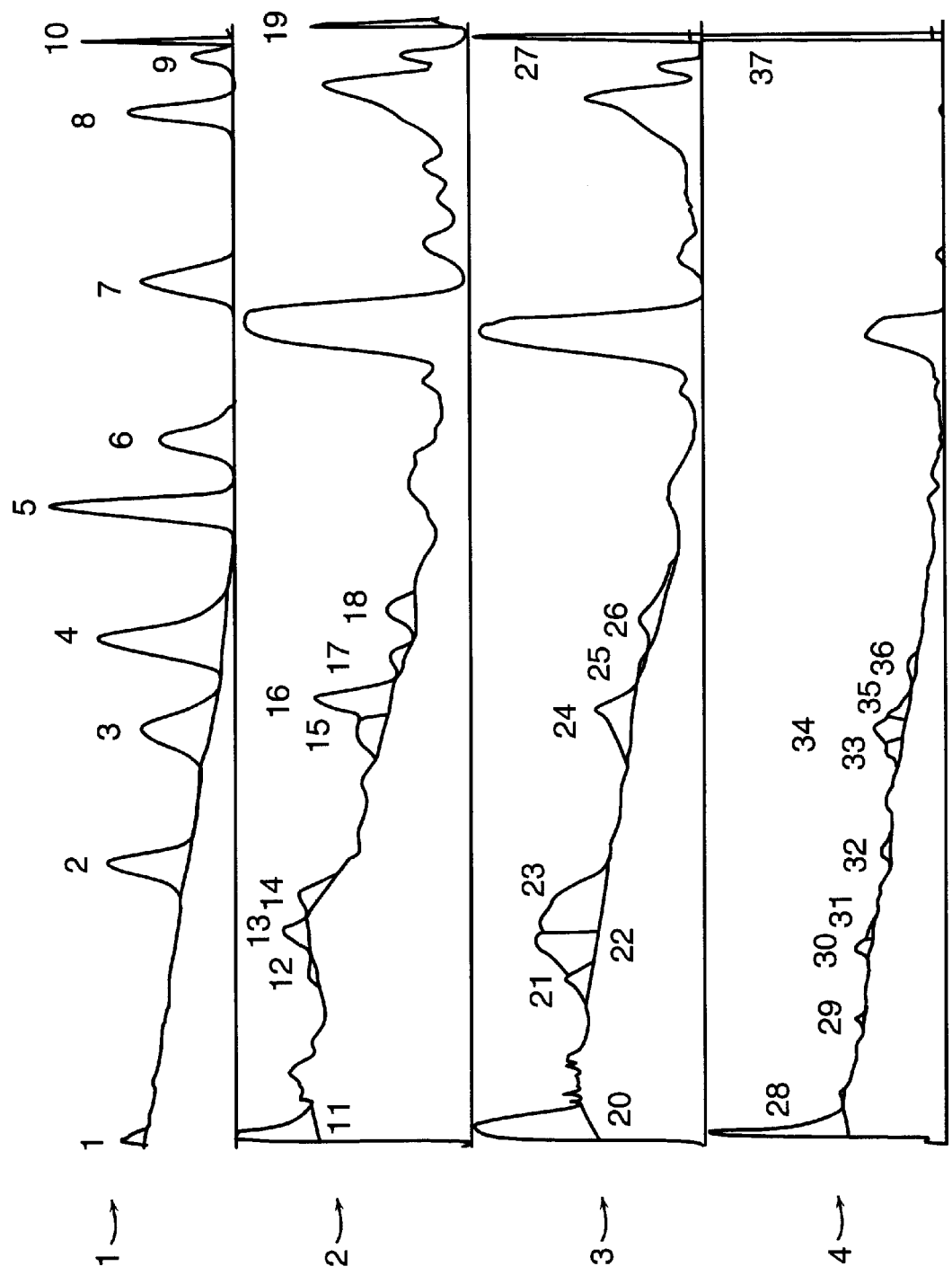
FIG. 3 is a densitometric representation of a Coomassie Blue stained sodium dodecyl sulfate (SDS) polyacrylamide gel in which lane 1 contains molecular weight markers, lane 2 contains crude Limulus amebocyte lysate, lane 3 contains precipitate removed from Limulus amebocyte lysate following the addition of a precipitating amount surfactant, and lane 4 contains amebocyte lysate supernatant produced after removal of the surfactant induced precipitate.

In FIG. 3, lane 1 represents the densitometric profile of molecular weight markers, wherein peak 2 represents a protein having a molecular weight of 66 kD, peak 3 represents a protein having a molecular weight of 45 kD, peak 4 represents a protein having a molecular weight of 36 kD, peak 5 represents a protein having a molecular weight of 29 kD, peak 6 represents a protein having a molecular weight of 24 kD, peak 7 represents a protein having a molecular weight of 20 kD, peak 8 represents a protein having a molecular weight of 14.2 kD, and peak 9 represents a protein having a molecular weight of 6.5 kD.

In FIG. 3, lane 2 represents a fractionated sample of crude amebocyte lysate wherein peaks 12 and 15 apparently represent the two subunits of Factor G (one having a molecular weight of about 76 kD and the other having a molecular weight of about 36 kD). Lane 3 represents a fractionated sample of amebocyte lysate supernatant following detergent precipitation. According to lane 3, it appears that the supernatant is depleted of the 76 kD and 36 kD Factor G subunits. Lane 4 represents a fractionated sample of the lysate precipitate. According to lane 4, it appears that the precipitate contains the 76 kD and 36 kD subunits of Factor G (peaks 29 and 33/34, respectively). According to these profiles, it appears that Factor G was actually precipitated from the lysate by the surfactant.

Example 2

Formulation of Amebocyte Lysate Depleted of Factor G Activity

Following preparation of the amebocyte lysate preparation of the invention, the resulting lysate was formulated as follows:

| COMPONENTS | PERCENTAGE OF COMPONENTS |
| --- | --- |
| Extracted Limulus Amebocyte Lysate | 37% |
| Water | 8% |
| 0.4 M $Mg^{2+}$/0.6 M Tris-HEPES Buffer | 10% |
| 6% Dextran | 6% |
| 3% NaCl | 39% |
| Laminarin | 0.000004%–0.000013% |

The resulting formulation was stored at 2–8° C. until use.

Example 3

Reactivity of Crude Amebocyte Lysate and Lysate Depleted of Factor G Activity with Bacterial Endotoxin This example demonstrates that amebocyte lysate of the invention still reacts with bacterial endotoxin, as determined by the gel-clot assay. Three batches of amebocyte lysate having reduced Factor G activity (referred to as L4941LB, L1081LB, L1711LB) as produced by the method of Example 1 and formulated as described in Example 2 were tested for endotoxin reactivity using a gel-clot assay. Batches L4941LB and L1081LB were also formulated with 0.4% bulking protein and 0.01% Zwittergent® 3–14.

The endotoxin reactivity of each batch of lysate was determined simultaneously with a control batch of lysate, referred to as reference lysate lot 13, obtained from the USFDA. The endotoxin standard used in each determination was obtained from USFDA, and is referred to herein as EC-6. Briefly, a standard solution of EC-6 endotoxin was prepared. Thereafter, endotoxin was added to the reference lysates to give a final endotoxin concentration of 0.5, 0.25, 0.125, 0.06, or 0.03 EU/mL. Similarly, endotoxin was added to the test lysates to give a final toxin concentration of 0.06, 0.03, 0.015, or 0.007 EU/mL. After mixing, the resulting mixtures were incubated at 37° C. for one hour, after which the presence or absence of a clot was noted. All the samples were treated the same.

In order to assure the integrity of the assay, the assays were performed in a specific order. For example, a first batch of four reference lysate samples (denoted by test number 1 in Tables 1, 3, and 5) was analyzed first, then a batch of ten lysate test samples formulated as described in Example 2 (denoted by vial numbers 1–10 in Tables 2, 4, and 6) was analyzed, and finally a second batch of four reference lysate samples (denoted by test number 2 in Tables 1, 3, and 5) was analyzed.

Each test sample was analyzed side-by-side with a reference lysate. Accordingly, data relating to the reactivity of reference lysate 13 (Table 1) was derived contemporaneously with data relating to the reactivity of the test lysate batch number L1711Lb (Table 2). According to Table 1, the reactivity of reference lysate 13 had an endpoint value (E.Pt) of 0.06 EU/niL for the assay (i.e., within a recognized acceptable level). According to Table 2, the reactivity of test lysate L1711LB (10 samples) had an endpoint value estimated at 0.06 EU/mL. Accordingly, the test lysate L1711LB was within an acceptable level of sensitivity.

TABLE 1

Reference Lysate Lot 13, Endotoxin Lot EC-6

| TEST | 0.5 | 0.25 | 0.125 | 0.06 | 0.03 | E.Pt. |
|------|-----|------|-------|------|------|-------|
| 1 | + | + | + | + | − | 0.06 |
| 1 | + | + | + | + | − | 0.06 |
| 1 | + | + | + | + | − | 0.06 |
| 1 | + | + | + | + | − | 0.06 |
| 2 | + | + | + | + | − | 0.06 |
| 2 | + | + | + | + | − | 0.06 |
| 2 | + | + | + | + | − | 0.06 |
| 2 | + | + | + | + | − | 0.06 |

MEAN (Log$_2$): −4
S.D. (Log$_2$ Data): —
Geometric Mean: 0.06
STATED ENDPOINT: 0.06 EU/ml

TABLE 2

Test Lysate Lot L 1711LB, Endotoxin Lot EC-6

| VIAL | 0.125 | 0.06 | 0.03 | 0.015 | E. Pt. |
|------|-------|------|------|-------|--------|
| 1 | + | + | − | − | 0.06 |
| 2 | + | + | − | − | 0.06 |
| 3 | + | + | − | − | 0.06 |
| 4 | + | + | − | − | 0.06 |
| 5 | + | + | − | − | 0.06 |
| 6 | + | + | − | − | 0.06 |
| 7 | + | + | − | − | 0.06 |
| 8 | + | + | − | − | 0.06 |
| 9 | + | + | − | − | 0.06 |
| 10 | + | + | − | − | 0.06 |

MEAN (Log$_2$): −4
S. D. (Log$_2$ Data): —
Geometric Mean: 0.06
STATED ENDPOINT: 0.06 EU/ml Similarly, data relating to the reactivity of reference lysate 13 (Table 3) was derived contemporaneously with data relating to the reactivity of the test lysate batch number L1081LB (Table 4). According to Table 3, the reactivity of reference lysate 13 had an endpoint value (E.Pt.) of 0.06 EU/mL for the assay (i.e., within a recognized acceptable level). According to Table 4, the reactivity of test lysate L1081LB (10 samples) had an endpoint value estimated at 0.015 EU/mL. Accordingly, the test lysate L1081LB was more sensitive to endotoxin than the reference lysate.

TABLE 3

Reference Lysate Lot 13, Endotoxin Lot EC-6

| TEST | 0.5 | 0.25 | 0.125 | 0.06 | 0.03 | E.Pt. |
|------|-----|------|-------|------|------|-------|
| 1 | + | + | + | + | − | 0.06 |
| 1 | + | + | + | + | − | 0.06 |
| 1 | + | + | + | + | − | 0.06 |
| 1 | + | + | + | + | − | 0.06 |
| 2 | + | + | + | + | − | 0.06 |
| 2 | + | + | + | + | − | 0.06 |
| 2 | + | + | + | + | − | 0.06 |
| 2 | + | + | + | + | − | 0.06 |

MEAN (Log$_2$): −4
S.D. (Log$_2$ Data): —
Geometric Mean: 0.06
STATED ENDPOINT: 0.06 EU/ml

TABLE 4

Test Lysate Lot L1081LB, Endotoxin Lot EC-6

| VIAL | 0.06 | 0.03 | 0.015 | 0.007 | E.PT. |
|------|------|------|-------|-------|-------|
| 1 | + | + | + | − | 0.015 |
| 2 | + | + | + | − | 0.015 |
| 3 | + | + | + | − | 0.015 |
| 4 | + | + | + | − | 0.015 |
| 5 | + | + | + | − | 0.015 |
| 6 | + | + | + | − | 0.015 |
| 7 | + | + | + | − | 0.015 |
| 8 | + | + | + | − | 0.015 |
| 9 | + | + | + | − | 0.015 |
| 10 | + | + | + | − | 0.015 |

MEAN (Log$_2$): −6
S.D. (Log$_2$ Data): —
Geometric Mean: 0.015
STATED ENDPOINT: 0.015 EU/ml In addition, data relating to the reactivity of reference lysate 13 (Table 5) was derived contemporaneously with data relating to the reactivity of the test lysate batch number L4941LB (Table 6). According to Table 5, the reactivity of reference lysate 13 had an endpoint value (E.Pt.) of 0.06 EU/mL for the assay (i.e., within a recognized acceptable level). According to Table 6, the reactivity of test lysate L4941LB (10 samples) had an endpoint value estimated at 0.03 EU/mL. Accordingly, the test lysate L4941LB was more sensitive to endotoxin than the reference lysate.

TABLE 5

Reference Lysate Lot 13, Endotoxin Lot EC-6

| TEST | 0.5 | 0.25 | 0.125 | 0.06 | 0.03 | E.Pt. |
|---|---|---|---|---|---|---|
| 1 | + | + | + | + | − | 0.06 |
| 1 | + | + | + | + | − | 0.06 |
| 1 | + | + | + | + | − | 0.06 |
| 1 | + | + | + | + | − | 0.06 |
| 2 | + | + | + | + | − | 0.06 |
| 2 | + | + | + | + | − | 0.06 |
| 2 | + | + | + | + | − | 0.06 |
| 2 | + | + | + | + | − | 0.06 |

MEAN ($Log_2$): −4
S.D. ($Log_2$ Data): —
Geometric Mean: 0.06
STATED ENDPOINT: 0.06 EU/ml

TABLE 6

Test Lysate Lot L4941LB, Endotoxin Lot EC-6

| VIAL | 0.06 | 0.03 | 0.015 | 0.007 | E.PT. |
|---|---|---|---|---|---|
| 1 | + | + | + | − | 0.015 |
| 2 | + | + | + | − | 0.015 |
| 3 | + | + | − | − | 0.03 |
| 4 | + | + | − | − | 0.03 |
| 5 | + | + | + | − | 0.015 |
| 6 | + | + | − | − | 0.03 |
| 7 | + | + | − | − | 0.03 |
| 8 | + | + | − | − | 0.03 |
| 9 | + | + | + | − | 0.015 |
| 10 | + | + | − | − | 0.03 |

MEAN ($Log_2$): −5.46
S.D. ($Log_2$ Data): 0.52
Geometric Mean: 0.02
STATED ENDPOINT: 0.03 EU/ml All three batches of lysate, L4941LB, L1081LB and L1711LB met the 24 hour negative control requirements as required by the USFDA.

Example 4

Reactivity of Crude Amebocyte Lysate and Lysate Depleted of Factor G Activity with Laminarin This example demonstrates that Limulus amebocyte lysates produced by the method of the invention, unlike crude lysates, are insensitive to the presence of laminarin in the sample. In addition, this example defines the optimal amount of laminarin (as determined from the crude lysate sample) that may be exogenously added to the lysate preparation of the invention, thereby to enhance the sensitivity of the lysate preparation to endotoxin.

A standard solution of laminarin was produced by dissolving 1.0 g of laminarin in 100 ml of 5 mM NaOH to produce a 10 mg/mL solution. The resulting solution was autoclaved at 121° C. for one hour. After autoclaving, the pH was adjusted to 7.0 with 0.1M Tris buffer. This solution was then diluted in pyrogen-free water to give a final laminarin stock solution of 0.2 mg/mnL. A dilution series of laminarin was produced, and the reactivity of crude lysate and the lysate preparation of the invention to laminarin was determined both by gel-clot and kinetic-turbidimetric assays.

I. Gel-clot Assay

Gel-clot assays were performed by combining either crude lysate or lysate preparations of the invention with different amounts of laminarin. Crude lysate (batch K2222L) was formulated essentially as described in Example 2, except that the "Extracted Limulus Amebocyte Lysate" was replaced with crude lysate and the concentration of laminarin was varied between samples. The lysate preparations of the invention (batch L4941LB, batch L1081LB, and batch L1711LB) were formulated essentially as described in Example 3, except the concentration of laminarin was varied between samples. The samples were incubated at 37° C., and the presence or absence of clots determined after one hour. Each experiment was performed in duplicate, and the results summarized in Table 7.

TABLE 7

| | | | LAMINARIN | | | | | |
|---|---|---|---|---|---|---|---|---|
| | | Conc. | K2222L | | L4941LB | | L1081LB | L1711LB |
| | Dilution | mg/mL | 0.03 | | 0.03 | | 0.015 | 0.06 |
| 1 | 50 | 4.00E−03 | − | − | − | − | − | − |
| 2 | 100 | 2.00E−03 | − | − | − | − | − | − |
| 3 | 200 | 1.00E−03 | − | − | − | − | − | − |
| 4 | 400 | 5.00E−04 | ▓ | ▓ | − | − | − | − |
| 5 | 800 | 2.50E−04 | ▓ | ▓ | − | − | − | − |
| 6 | 1600 | 1.25E−04 | ▓ | ▓ | − | − | − | − |
| 7 | 3200 | 6.25E−05 | ▓ | ▓ | − | − | − | − |
| 8 | 6400 | 3.13E−05 | ▓ | ▓ | − | − | − | − |
| 9 | 12800 | 1.56E−05 | − | − | − | − | − | − |
| 10 | 25600 | 7.81E−06 | − | − | − | − | − | − |
| 11 | 51200 | 3.91E−06 | − | − | − | − | − | − |
| 12 | 102400 | 1.95E−06 | − | − | − | − | − | − |
| 13 | 204800 | 9.77E−07 | − | − | − | − | − | − |
| 14 | 409600 | 4.88E−07 | − | − | − | − | − | − |
| 15 | 819200 | 2.44E−07 | − | − | − | − | − | − |
| 16 | 1638400 | 1.22E−07 | − | − | − | − | − | − |
| 17 | 3276800 | 6.10E−08 | − | − | − | − | − | − |
| 18 | 6553600 | 3.05E−08 | − | − | − | − | − | − |

Shaded areas represent sample active range.

The results in Table 7 indicate that none of the batches produced by the method of the invention (i.e., L4941LB, L1081LB and L1711LB) were reactive with exogenously added laminarin. In contrast, the batch of crude lysate (K2222L) was reactive with laminarin over the dilution range of 400 through 6400 in a gel-clot assay.

II. Kinetic-turbidimetric Assay

Reactions were initiated by combining either formulated crude lysate (batch K2222L) or formulated lysate preparations of the invention (batch L4941LB, batch 1081LB, and batch L1711LB) with different amounts of laminarin. The assay was formed using a Biotek elx-808 incubating nicroplate reader in accordance with the manufacturers instructions. Each assay was run, at least, in duplicate. During the assay, the samples were incubated at 37±0.2° C., and data was collected over a period of one hour.

The assay was performed simultaneously using additional lysate samples incubated in the presence of known amounts of endotoxin standards. Endotoxin standards were used to generate a standard curve covering a 4-log range, for example, from 50 to 0.005 EU/mL. After data collection, the data was analyzed using Biotek Kc3-cre kinetic software (available from Charles River Endosafe, Charleston, S.C.). The sample concentrations were interpreted as "endotoxin values" by the instrument and were represented by the units of EU/mL because they were estimated from the endotoxin standard curve. The resulting concentration values reflect the reactivity of the lysate to laminarin, and are referred to as "endotoxin equivalent values".

By plotting the laminarin endotoxin equivalent values versus dilution factor, it is possible to generate a bell-shaped curve with crude lysate. The peak of the curve provides the optimal amount of laminarin which can be added to amebocyte lysate depleted of Factor G activity, thereby to enhance the sensitivity of the lysate.

Figure 4:
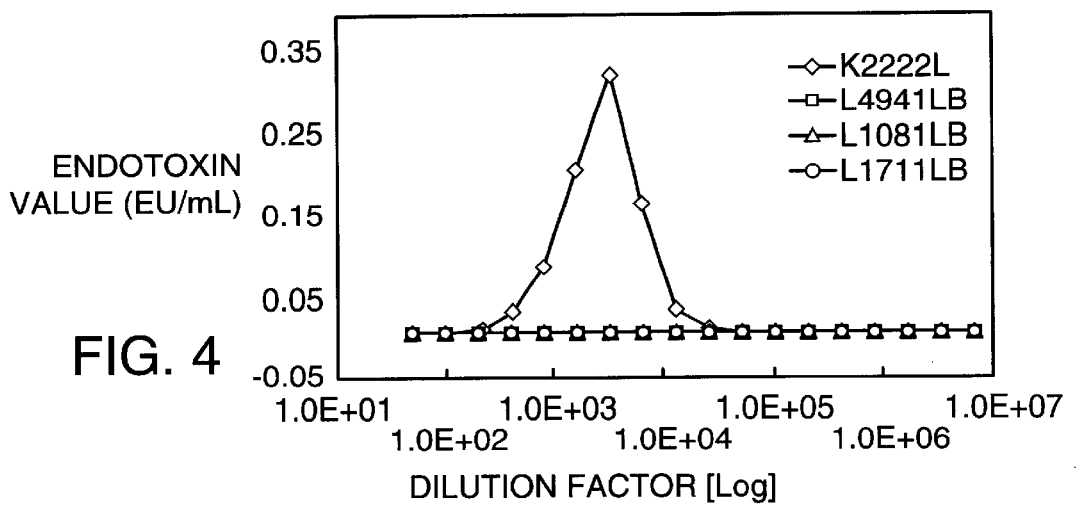
FIG. 4 is a graph showing the reactivity with laminarin of crude Limulus amebocyte lysate and Limulus amebocyte lysate of the invention. Diamonds represent batch K2222L, squares represent batch L4941LB, triangles represent batch L1081LB, and circles represent batch L1711LB.

The results of the experiment are shown in FIG. 4. According to FIG. 4, none of the batches produced by the method of the invention (i.e., L4941LB, L1081LB and L1711LB) were reactive with exogenously added laminarin. In contrast, the batch of crude lysate (K2222L) was reactive with laminarin over the dilution range of 100 through 51200, with the dilution value of 3200 producing the maximal endotoxin equivalent value. Accordingly, this value represents the optimal amount of laminarin to be added to amebocyte lysate depleted of Factor G activity to provide maximal sensitivity to endotoxin in a kinetic turbidimetric assay.

Example 5

Reactivity of Crude Amebocyte Lysate and Lysate Depleted of Factor G Activity with LAL Reactive Material This example demonstrates that Limulus amebocyte lysates produced by the method of the invention, unlike crude lysates, are insensitive to the presence in the sample of LAL reactive material (LAL-RM) produced by rinsing a cellulose-acetate filter with water. In addition, this example defines the optimal amount of this LAL-RM (as determined from the crude lysate sample) that may be exogenously added to the lysate preparation of the invention, thereby to enhance the sensitivity of the lysate preparation to endotoxin.

LAL-RM was prepared by passing one liter of pyrogen-free water through a conventional sterile, non-pyrogenic cellulose acetate hollow fiber membrane adapted for use in renal dialysis. The resulting rinse then was used to create a dilution series of cellulose acetate rinse. The reactivity of crude lysate and the lysate preparation of the invention to the cellulose acetate rinse was determined both by gel-clot and kinetic-turbidimetric assays.

I. Gel-clot Assay

The gel-clot assays were performed as described in Example 4I above, except in the formulations laminarin was replaced by cellulose acetate rinse. The assays were performed by combining either formulated crude lysate (batch K2222L) or formulated lysate preparations of the invention (batch L4941LB, batch L1081LB, and batch L1711LB) with different amounts of cellulose acetate rinse. The samples were incubated at 37° C., and the presence or absence of clots assessed after one hour. Each experiment was performed in duplicate and the results summarized in Table 8.

TABLE 8

Cellulose Acetate Rinse

| Dilution | Conc. mg/mL | K2222L 0.03 | L4941LB 0.03 | L1081LB 0.015 | L1711LB 0.06 | | |
|---|---|---|---|---|---|---|---|
| 1 | 50 | 4.00E–03 | ▨ | – | – | – | – |
| 2 | 100 | 2.00E–03 | ▨ | – | – | – | – |
| 3 | 200 | 1.00E–03 | ▨ | – | – | – | – |
| 4 | 400 | 5.00E–04 | ▨ | – | – | – | – |
| 5 | 800 | 2.50E–04 | ▨ | – | – | – | – |
| 6 | 1600 | 1.25E–04 | ▨ | – | – | – | – |
| 7 | 3200 | 6.25E–05 | ▨ | – | – | – | – |
| 8 | 6400 | 3.13E–5 | ▨ | – | – | – | – |
| 9 | 12800 | 1.56E–05 | – | – | – | – | – |
| 10 | 25600 | 7.81E–06 | – | – | – | – | – |
| 11 | 51200 | 3.91E–06 | – | – | – | – | – |
| 12 | 102400 | 1.95E–06 | – | – | – | – | – |
| 13 | 204800 | 9.77E–07 | – | – | – | – | – |
| 14 | 409600 | 4.88E–07 | – | – | – | – | – |
| 15 | 819200 | 2.44E–07 | – | – | – | – | – |
| 16 | 1638400 | 1.22E–07 | – | – | – | – | – |
| 17 | 3276800 | 6.10E–08 | – | – | – | – | – |
| 18 | 6553600 | 3.05E–08 | – | – | – | – | – |

Shaded areas represent sample active range.

The results of Table 8 indicate that none of the batches produced by the method of invention (i.e., LA4941LB, L1081LB and L1711LB) were reactive with exogenously added cellulose acetate rinse as determined by gel-clot assay. In contrast, the batch of crude lysate (K2222L) was reactive with cellulose acetate over the dilution range of 50 ugh 6400 in a gel-clot assay.

II. Kinetic-turbidimetric Assay

Figure 5:
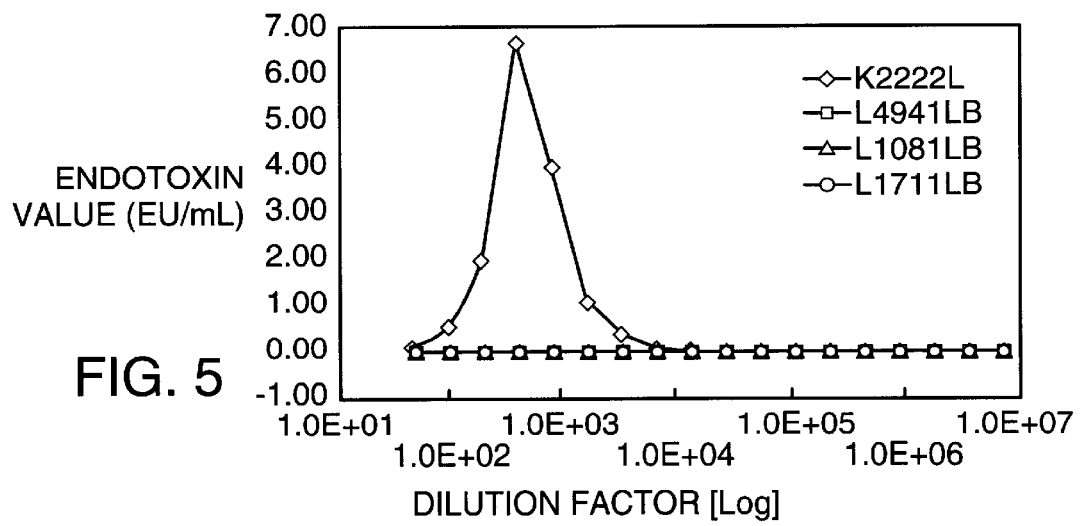
FIG. 5 is a graph showing the reactivity with a cellulose acetate rinse of crude Limulus amebocyte lysate and Limulus amebocyte lysate of the invention. Diamonds represent batch K2222L, squares represent batch L4941LB, triangles represent batch L1081LB, and circles represent batch L1711LB.

This assay was performed as described in Example 4II above, except in the formulations laminarin was replaced by cellulose acetate rinse. Reactions were initiated by combining either crude lysate (batch K2222L) or lysate preparations of the invention (batch L4941LB, batch L1081LB, and batch L1711LB) with different amounts of cellulose acetate rinse. The results of the assay are presented in FIG. 5. According to FIG. 5, none of the batches produced by the method of the invention (i.e., LA4941LB, L1081LB and L1711LB) were reactive with exogenously added cellulose acetate. In contrast, the batch of crude lysate (K2222L) was reactive with cellulose acetate over the dilution range of 50 through 102400 with the dilution value of 400 producing the maximal endotoxin equivalent value. Accordingly, this value represents the optimal amount of cellulose acetate to be added to amebocyte lysate depleted of Factor G activity to provide maximal sensitivity to endotoxin in a kinetic turbidimetric assay.

Example 6

Reactivity of Crude Amebocyte Lysate and Lysate Depleted of Factor G Activity with Cotton Extract This example demonstrates that Limulus amebocyte lysates produced by the method of the invention, unlike crude lysates, are insensitive to the presence in the sample of cotton extract. In addition, this example defines the optimal amount of cotton extract (as determined from the crude lysate sample) that may be exogenously added to the lysate preparation of the invention, thereby to enhance the sensitivity of the lysate preparation to endotoxin.

Cotton extract was prepared as follows. Approximately, 1 gram of cotton (about 4 one inch cotton balls) was added to 40 ml of 1 N NaOH in a 50 ml polystyrene conical tube. Thereafter, the mixture was incubated at room temperature (about 20° C.) for 10 days. Prior to use, the solution was decanted from the cotton into a fresh, pyrogen-free tube (baked 200° C., 6 h) and neutralized with HCl to produce a stock solution of cotton extract. Further dilutions were made in pyrogen-free water (available from Charles River Endosafe, Charleston, S.C.). The reactivity of crude lysate and the lysate preparation of the invention to cotton extract were determined both by gel-clot and kinetic-turbidimetric assays.

I. Gel-clot Assay

The gel-clot assays were performed as described in Example 4I above, except in the formulations laminarin was replaced by cotton extract. The assays were performed by combining either formulated crude lysate (batch K2222L) or formulated lysate preparations of the invention (batch L4941LB, batch L1081LB, and batch L1711LB) with different amounts of cotton extract. The samples were incubated at 37° C., and the presence or absence of clots determined after one hour. Each experiment was performed in duplicate and the results summarized in Table 9.

TABLE 9

COTTON EXTRACT

| Dilution | Conc. mg/mL | K2222L 0.03 | | L4941LB 0.03 | | L1081LB 0.015 | | L1711LB 0.06 | |
| --- | --- | --- | --- | --- | --- | --- | --- | --- | --- |
| 1 | 50 | 4.00E-03 | / | / | / | / | / | / | / |
| 2 | 100 | 2.00E-03 | ▓ | − | − | − | − | − | − |
| 3 | 200 | 1.00E-03 | ▓ | − | − | − | − | − | − |
| 4 | 400 | 5.00E-04 | ▓ | − | − | − | − | − | − |
| 5 | 800 | 2.50E-04 | ▓ | − | − | − | − | − | − |
| 6 | 1600 | 1.25E-04 | − | − | − | − | − | − | − |
| 7 | 3200 | 6.25E-05 | − | − | − | − | − | − | − |
| 8 | 6400 | 3.13E-05 | − | − | − | − | − | − | − |
| 9 | 12800 | 1.56E-05 | − | − | − | − | − | − | − |
| 10 | 25600 | 7.81E-06 | − | − | − | − | − | − | − |
| 11 | 51200 | 3.91E-06 | − | − | − | − | − | − | − |
| 12 | 102400 | 1.95E-06 | − | − | − | − | − | − | − |
| 13 | 204800 | 9.77E-07 | − | − | − | − | − | − | − |
| 14 | 409600 | 4.88E-07 | − | − | − | − | − | − | − |
| 15 | 819200 | 2.44E-07 | − | − | − | − | − | − | − |
| 16 | 1638400 | 1.22E-07 | − | − | − | − | − | − | − |
| 17 | 3276800 | 6.10E-08 | − | − | − | − | − | − | − |
| 18 | 6553600 | 3.05E-08 | − | − | − | − | − | − | − |

Shaded areas represent sample active range.

The results in Table 8 indicate that none of the batches produced by the method of the invention (i.e., L4941LB, L1081LB and L1711LB) were reactive with exogenously added cotton extract. In contrast, the batch of crude lysate (K2222L) was reactive with cotton extract over the dilution range of 100 through 800 in a gel-clot assay.

II. Kinetic-turbidimetric Assay

Figure 6:
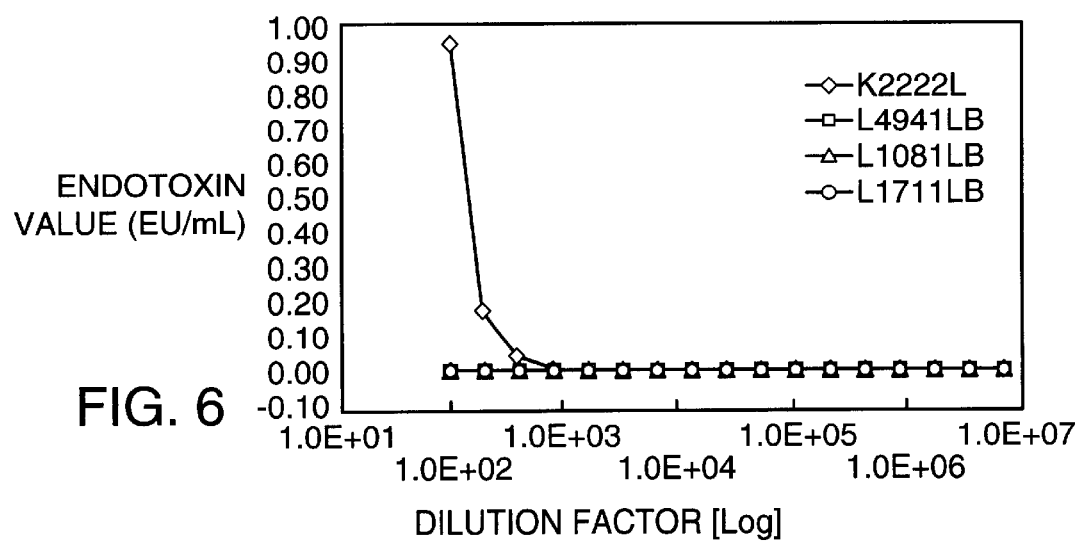
FIG. 6 is a graph showing the reactivity with cotton extract of crude Limulus amebocyte lysate and Limulus amebocyte lysate of the invention. Diamonds represent batch K2222L, squares represent batch L4941LB, triangles represent batch L1081LB, and circles represent batch L1711LB.

This assay was performed as described in Example 4II above, except in the formulations laminarin was replaced by cotton extract. Reactions were initiated by combining either crude lysate (batch K2222L) or lysate preparations of the invention (batch L4941LB, batch L1081LB, and batch L1711 LB) with different amounts of cotton extract. The results of the assay are presented in FIG. 6. According to FIG. 6, none of the batches produced by the method of the invention (i.e., L4941LB, L1081LB and L1711LB) were reactive with exogenously added cotton extract. In contrast, the batch of crude lysate (K2222L) was reactive with cotton extract over the dilution range of from at least 100 through 3200. According to the results, it appears that cotton extract also may be used to enhance the sensitivity of Factor G depleted lysate to endotoxin.

Example 7

Endotoxin Sensitivity of Amebocyte Lysate Depleted of Factor G Activity With and Without (1→3)-β-D Glucan This example demonstrates that the sensitivity to endotoxin of an amebocyte lysate depleted of Factor G activity can be enhanced by the addition of exogenous (1→3)-β-D glucan.

Figure 7:
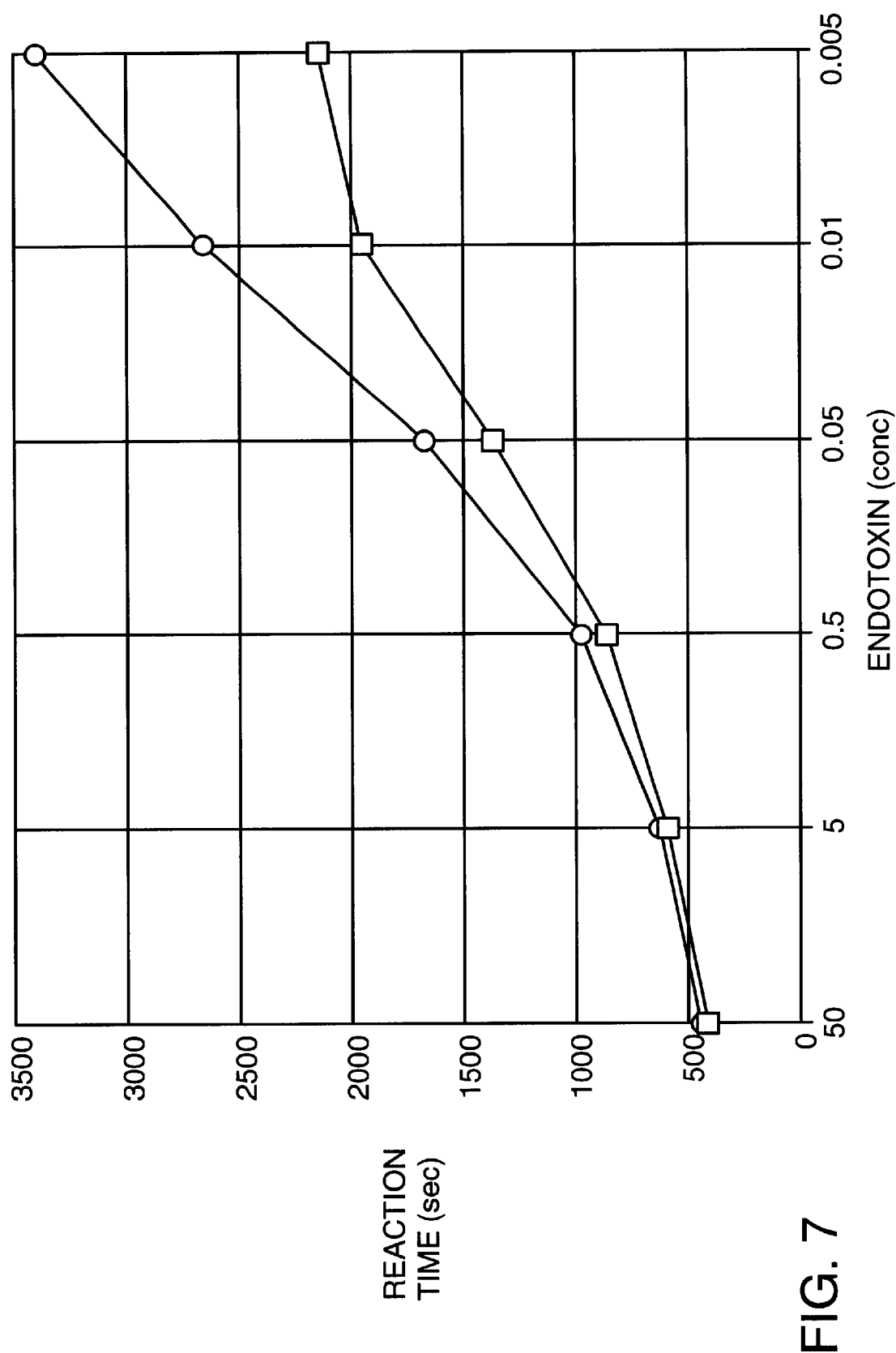
FIG. 7 is a graph showing the sensitivity to endotoxin of Limulus amebocyte lysate of the invention in the presence and absence of exogenously added (1→3)-β-D glucan. The circles represent lysate without exogenously added laminarin and the boxes represent lysate with exogenously added laminarin.

Briefly a batch of amebocyte lysate prepared in accordance with Example 1 was formulated essentially as described in Example 2. A control batch was formulated without the exogenously added laminarin. The reactivities of each lysate to different amounts of endotoxin were measured by kinetic-turbidimetric assay, essentially as described in Example 4II. Briefly, different amounts of endotoxin (USFDA lot EC-6) were added to each sample of lysate and the reaction end point determined by Bio-tek KC3-cre kinetic software. The results are shown in FIG. 7. The circles represent samples of lysate not supplemented with laminarin (control samples), and the boxes represent samples of lysate supplemented with laminarin (test samples).

According to FIG. 7, at high concentrations of endotoxin (i.e., about 50 EU/ml) there appears to be little difference in reaction time between lysate supplemented with laminarin and lysate not supplemented with laminarin. However, at low concentrations of endotoxin (i.e., about ≤0.05 EU/mL), the lysate supplemented with laminarin reacted significantly faster with endotoxin than lysate not supplemented with larinarin. Accordingly, these results demonstrate that it is possible to enhance the sensitivity of an amebocyte lysate depleted of Factor G activity by the addition of exogenous (1→3)-β-D glucan.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of producing an improved amebocyte lysate preparation having reduced Factor G activity, the method comprising the steps of:

(a) admixing crude amebocyte lysate with an ionic surfactant in an amount sufficient to produce a solution containing a precipitate; and (b) separating said precipitate from said solution thereby to produce an amebocyte lysate preparation which is less reactive with (1→3)-β-D glucan than said crude amebocyte lysate.

2. The method of claim 1, wherein said amebocyte lysate preparation is reactive with a bacterial endotoxin.

3. The method of claim 1 or 2, wherein said precipitate contains Factor G.

4. The method of claim 1 or 2, wherein said ionic surfactant is a zwitterionic surfactant.

5. The method of claim 4, wherein said zwitterionic surfactant is a sulfobetaine-type surfactant.

6. The method of claim 5, wherein said sulfobetaine-type surfactant is selected from the group consisting of n-octyl-N, N-dimethyl-3-ammonio-1-propanesulfonate, n-decyl-N, N-dimethyl-3-ammonio-1-propanesulfonate, n-dodecyl-N, N-dimethyl-3-ammonio-1-propanesulfonate, n-tetradecyl-N, N-dimethyl-3-ammonio-1-propanesulfonate, and n-hexadecyl-N, N-dimethyl-3-ammonio-1-propanesulfonate.

7. The method of claim 5, wherein said sulfobetaine-type surfactant is n-tetradecyl-N, N-dimethyl-3-ammonio-1-propanesulfonate.

8. The method of claim 1, comprising the additional step of removing said ionic surfactant from said solution.

9. The method of claim 8, wherein said ionic surfactant is removed by organic solvent extraction.

10. The method of claim 9, wherein said organic solvent is chloroform.

11. A method of producing an improved amebocyte lysate preparation having reduced Factor G activity, the method comprising the steps of:
  (a) admixing crude amebocyte lysate with a zwitterionic surfactant in an amount sufficient to produce a solution containing a precipitate; and
  (b) removing said precipitate from said solution thereby to produce an amebocyte lysate preparation which is less reactive with $(1 \rightarrow 3)$-$\beta$-D glucan than said crude amebocyte lysate.

12. The method of claim 11, wherein said amebocyte lysate preparation reacts with a bacterial endotoxin.

13. The method of claim 11, wherein said precipitate contains Factor G.

14. The method of claim 11, wherein said zwitterionic surfactant is a sulfobetaine-type surfactant.

15. The method of claim 14, wherein said sulfobetaine-type surfactant is selected from the group consisting of n-octyl-N, N-dimethyl-3-ammonio-1-propanesulfonate, n-decyl-N, N-dimethyl-3-ammonio-1-propanesulfonate, n-dodecyl-N, N-dimethyl-3-ammonio-1-propanesulfonate, n-tetradecyl-N, N-dimethyl-3-ammonio-1-propanesulfonate, and n-hexadecyl-N, N-dimethyl-3-ammonio-1-propanesulfonate.

16. The method of claim 14, wherein said sulfobetaine surfactant is n-tetradecyl-N, N-dimethyl-3-ammonio-1-propanesulfonate.

17. The method of claim 11, comprising the additional step of removing said zwitterionic surfactant from said solution.

18. The method of claim 17, wherein said zwitterionic surfactant is removed by organic solvent extraction.

19. The method of claim 18, wherein said organic solvent is chloroform.

20. A method of producing an improved amebocyte lysate having reduced Factor G activity, the method comprising the steps of:
  (a) admixing crude amebocyte lysate with a n-tetradecyl-N, N-dimethyl-3-ammonio-1-propanesulfonate surfactant in an amount sufficient to produce a solution containing a precipitate;
  (b) separating said precipitate from said solution; and
  (c) removing said n-tetradecyl-N, N-dimethyl-3-ammonio-1-propanesulfonate surfactant from said solution thereby to produce an amebocyte lysate preparation that is reactive with bacterial endotoxin and is less reactive with $(1 \rightarrow 3)$-$\beta$-D glucan than said crude amebocyte lysate.

21. The method of claim 20, wherein said n-tetradecyl-N N-dimethyl-3-ammonio-1-propanesulfonate surfactant is removed by organic solvent extraction.

22. The method of claim 21, wherein said organic solvent is chloroform.

23. The method of claim 2, 12, or 20 comprising the additional step of, after step (b) of claim 2 or 12 or after step (c) of claim 20, adding exogenous $(1 \rightarrow 3)$-$\beta$-D glucan to said amebocyte lysate preparation in an amount sufficient to enhance the sensitivity of said amebocyte lysate preparation to said endotoxin relative to said amebocyte lysate preparation without said exogenous $(1 \rightarrow 3)$-$\beta$-D glucan.

24. The method of claim 23, wherein said exogenous $(1 \rightarrow 3)$-$\beta$-D glucan is selected from the group consisting of LAL-RM, curdlan, pachyman, scleratan, leutinan, schizophyllan, coriolan, laminaran, and laminarin.

25. The method of claim 23, wherein said $(1 \rightarrow 3)$-$\beta$-D glucan is laminarin.

26. An amebocyte lysate preparation produced by the method of claim 23.

27. In an amebocyte lysate-based method of detecting a bacterial endotoxin in a sample, the improvement comprising using the amebocyte lysate preparation of claim 26.

* * * * *